United States Patent
Cimermancic

(10) Patent No.: US 12,362,041 B1
(45) Date of Patent: Jul. 15, 2025

(54) METHODS AND SYSTEMS FOR USING MACHINE-LEARNING MODELS TO ESTIMATE PEPTIDE-RETENTION TIME

(71) Applicant: Verily Life Sciences LLC, South San Francisco, CA (US)

(72) Inventor: Peter Cimermancic, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1049 days.

(21) Appl. No.: 16/459,052

(22) Filed: Jul. 1, 2019

Related U.S. Application Data

(60) Provisional application No. 62/699,973, filed on Jul. 18, 2018.

(51) Int. Cl.

| | |
|---|---|
| G16B 40/00 | (2019.01) |
| G01N 30/86 | (2006.01) |
| G01N 30/88 | (2006.01) |
| G06N 3/08 | (2023.01) |
| G06N 20/10 | (2019.01) |
| G16B 35/00 | (2019.01) |

(52) U.S. Cl.
CPC ......... *G16B 40/00* (2019.02); *G01N 30/8693* (2013.01); *G01N 30/88* (2013.01); *G06N 3/08* (2013.01); *G06N 20/10* (2019.01); *G16B 35/00* (2019.02); *G01N 2030/8831* (2013.01)

(58) Field of Classification Search
CPC ........ G16B 40/00; G16B 35/00; G06N 20/10; G06N 3/08; G01N 30/8693; G01N 30/88; G01N 2030/8831
See application file for complete search history.

(56) References Cited

U.S. PATENT DOCUMENTS

2010/0161530 A1* 6/2010 Petritis ............... G01N 33/6806
706/12

FOREIGN PATENT DOCUMENTS

WO WO-2018213112 A1 * 11/2018

OTHER PUBLICATIONS

Wolfer et al. 2016. UPLC-MS retention time prediction: a machine learning approach to metabolite identification in untargeted profiling. Metabolomics 12:8. DOI 10.1007/s11306-015-0888-2 (Year: 2016).*
Heffernan et al. 2017. Capturing non-local interactions by long short-term memory bidirectional recurrent neural networks for improving prediction of protein secondary structure, backbone angles, contact Nos. and solvent accessibility. Bioinformatics 33(18), 2842-2849. (Year: 2107).*
Blazenovic I. Software tools and approaches for compound identification of LC-MS/MS data in metabolomics. Metabolites 8(31): 1-23. (Year: 2018).*
Agilent Technologies. Sample Preparation Fundamentals for Chromatography. 364 pages. (Year: 2013).*
Klammer AA. Improving tandem mass spectrum identification using peptide retention time prediction across diverse chromatographic conditions. Analytical Chemistry 79: 6111-6118. (Year: 2007).*
Pfeifer N. Statistical learning of peptide retention behavior in chromatographic separations: a new kernel-based approach for computational proteomics. BMC Bioinformatics 8:468, 1-14. (Year: 2007).*
"Advancing precision medicine: Current and future proteogenomic strategies for biomarker discovery and development", A Sponsored Supplement to Science, Oct. 13, 2017, 40 pages.
"Peptide", Wikipedia, accessed via internet on Jun. 28, 2018 at https://en.wikipedia.org/w/index.php?title=Peptide&oldid=843788818, 6 pages.
Aebersold et al., "Mass-spectrometric exploration of proteome structure and function", Nature, vol. 537, Sep. 15, 2016, pp. 347-355.
Brownlee , "Sequence Classification with LSTM Recurrent Neural Networks in Python with Keras", Natural Language Processing, Jul. 26, 2016, 104 pages.
Karpathy , "The Unreasonable Effectiveness of Recurrent Neural Networks", Hacker's Guide to Neural Networks, May 21, 2015, 39 pages.
Lu et al., "Locus-specific Retention Predictor (LsRP): A Peptide Retention Time Predictor Developed for Precision Proteomics", Scientific Reports, 7:43959, Mar. 17, 2017, 9 pages.
Ma et al., "DeepRT: deep learning for peptide retention time prediction in prote-omics", 2017, 2 pages.
Simm et al., "50 years of amino acid hydrophobicity scales: revisiting the capacity for peptide classification", Biological Research, 49:31, 2016, 19 pages.

(Continued)

*Primary Examiner* — Olivia M. Wise
*Assistant Examiner* — Robert J. Kallal
(74) *Attorney, Agent, or Firm* — Kilpatrick Townsend & Stockton LLP

(57) ABSTRACT

The present disclosure relates to a machine-learning computing system for training and running a machine-learning model to estimate peptide-retention time for a sample. The machine-learning model can be configured to process inputs that characterize an individual peptide and/or amino acids in the peptide and to output an estimated retention time within a liquid-chromatography column for the peptide. The machine-learning model can include an encoder-decoder model. The encoder and/or the decoder can include a neural network. A subset of peptides can then be identified that are associated with estimated retention times within a specific elution time period during which portion of the sample was eluted from a chromatography column, and mass-spectrometry data can be analyzed to determine which of the subset of peptides are present within the sample.

17 Claims, 6 Drawing Sheets

(56) References Cited

OTHER PUBLICATIONS

Spicer et al., "Sequence-Specific Retention Calculator. A Family of Peptide Retention Time Prediction Algorithms in Reversed-Phase HPLC: Applicability to Various Chromatographic Conditions and Columns", Analytical Chemistry, vol. 79, No. 22, Nov. 15, 2007, pp. 8762-8768.

* cited by examiner

METHODS AND SYSTEMS FOR USING MACHINE-LEARNING MODELS TO ESTIMATE PEPTIDE-RETENTION TIME

CROSS-REFERENCE TO RELATED APPLICATION

This application claims the benefit of and the priority to U.S. Provisional Application No. 62/699,973, filed on Jul. 18, 2018, which is hereby incorporated by reference in its entirety for all purposes.

FIELD

The present disclosure relates to using a machine-learning model to facilitate peptide detection within samples. More specifically, the present disclosure relates to training a machine-learning model using training data that identifies amino-acid characteristics and retention times of a first set of peptides, and executing the trained machine-learning model to estimate retention times of a second set of peptides. A subset of peptides can then be identified that are associated with estimated retention times within a specific elution time period during which portion of the sample was eluted from a chromatography column, and mass-spectrometry data can be analyzed to determine which of the subset of peptides are present within the sample.

BACKGROUND

Proteomics involve the broad and systematic analysis of proteins, which includes their identification, quantification, and ultimately the attribution of one or more biological functions. Proteomic analyses are challenging due to the high complexity and dynamic range of peptide abundances. It is frequently advantageous to perform systematic analysis of expressed peptides in a high-throughput manner and with high sensitivity, further increasing the challenge. As a result, recent efforts have focused on improving separation speed, resolving power and dynamic range. These techniques have generally been based on the combination of separations with mass spectrometry (MS), by correlating tandem mass spectra with established protein databases. However, these techniques are limited by the finite size of the databases and by interactions between signals when a sample includes multiple proteins.

BRIEF SUMMARY

In some embodiments, a method for estimating peptide-retention time is provided. Training data is accessed by a machine-learning model. The training data includes a plurality of training data sets. Each training data set of the plurality of training data sets correspond to a peptide. Each training data set of the plurality of training data sets includes one or more training vectors that indicate, for each amino acid present in the peptide, an identity or characteristic of the amino acid and a retention time for the peptide. The retention time may correspond to a duration of time for the peptide to elute from a separations column. The machine-learning model is trained with the training data. The machine-learning model includes an encoder-decoder network including an encoder portion and a decoder portion. The encoder portion includes a recurrent neural network. One or more other data sets are received. Each of the one or more other data sets represent another peptide. Each of the one or more other data sets includes one or more input vectors that indicate, for each amino acid present in the other peptide, an identity or characteristic of the amino acid. For each of the one or more other data sets, one or more input vectors of the other data set is processed using the machine learning model to output an estimated retention time for the other peptide. A retention-time library is built by storing, for each other data set of the one or more other data sets, an identifier of the peptide represented by the other data set in association with the estimated retention time corresponding to the other data set.

In some embodiments, a computer-program product is provided that is tangibly embodied in a non-transitory machine-readable storage medium. The computer-program product can include instructions configured to cause one or more data processors to perform operations of part or all of one or more methods disclosed herein.

In some embodiments, a system is provided that includes one or more data processors and a non-transitory computer readable storage medium containing instructions which, when executed on the one or more data processors, cause the one or more data processors to perform operations of part or all of one or more methods disclosed herein.

BRIEF DESCRIPTION OF THE DRAWINGS

The present invention will be better understood in view of the following non-limiting figures, in which.

DETAILED DESCRIPTION

Figure 1:
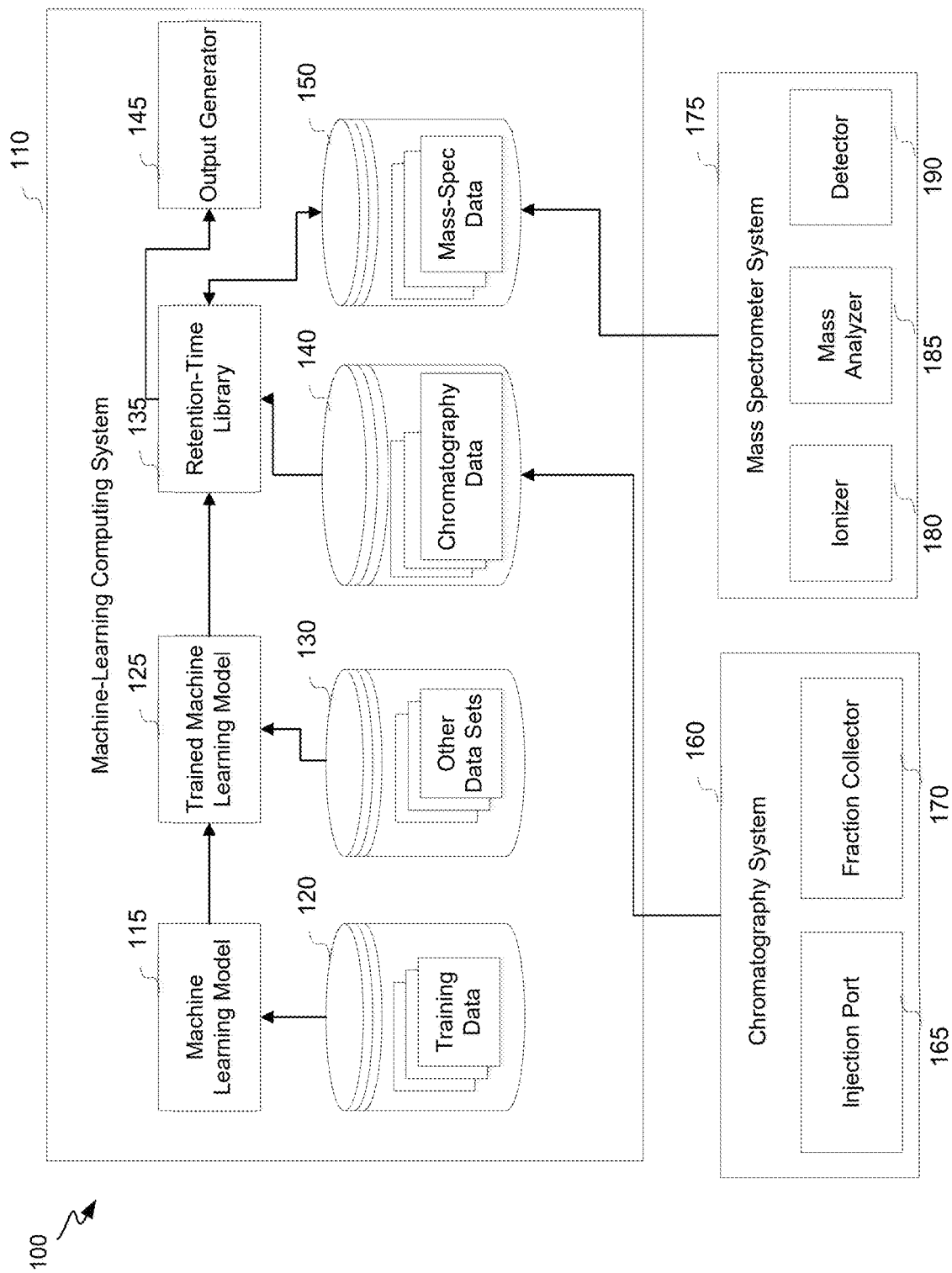
FIG. 1 shows a system for estimating peptide-retention for a sample in accordance with some embodiments of the invention.

In some embodiments, a machine-learning computing system is provided for training and running a machine-learning model. The machine-learning model can be configured to process inputs that characterize an individual peptide and/or amino acids in the peptide and to output an estimated retention time within a liquid-chromatography column for the peptide. The machine-learning model can include an encoder-decoder model. The encoder and/or the decoder can include a neural network. A neural network in the encoder can include a recurrent neural network and one or more long-short term memory (LSTM) cells configured to process ordered information. A neural network in the decoder can include a dense network, such as a fully-connected network. In some instances, one or both of the encoder and decoder includes multiple layers. For example, the encoder may include between two and five layers, and the decoder may also include between two and five layers.

The machine-learning model can be trained with a plurality of training data sets. Each of the plurality of training data sets can correspond to a peptide and include amino-acid data that indicates an identity (i.e., type of amino acid) or characteristic (e.g., hydrophobicity) of each amino acid present in the peptide. Each of the plurality of training data sets can further include retention time for the peptide that indicates how long it takes for the peptide to elute from a separations column (e.g., liquid chromatography column) relative to an injection time. The machine-learning model may be configured (e.g., prior to a learning process) with a set of hyperparameters (e.g., that are not configured to be derived based on training data), such as a learning rate, number of nodes, number of layers, Kernel/filter size, padding size, stride, number of channels, and/or pooling-layer parameters. Training the machine-learning model can include using supervised or semi-supervised learning to derive values for each of a set of parameters (e.g., values for LSTM gates, bias neurons, inter-neuron weights, etc.).

The trained machine-learning model can then be used to estimate peptide-retention times for other peptides. For example, the trained machine-learning model can receive one or more other data sets—each representing another peptide. Each of the other data sets can include amino-acid data that indicates, for each amino acid present in the other peptide, an identity or characteristic of the amino acid. The trained machine-learning model can process the other data sets to output an estimated retention time for each of the other peptides. A retention-time library can be built or updated to include, for each of the other data sets, an association between an identifier of the peptide represented by the other data set and the estimated retention time. The retention-time library may further include associations between peptide identifiers and retention times from the training data sets.

The retention-time library can be used to detect one or more peptides within a sample using one or more mass spectra generated using the sample. More specifically, a sample can be injected into a chromatography column. Different parts of the sample may be eluted from the column at different times, which can occur as a result of different peptides within the sample being fractionated at different times within in the chromatography column. A portion of the sample that is eluted from the chromatography column can be collected and associated with an elution time period indicating when the portion was eluted from the column relative to a sample-injection time. The retention-time library can be queried to identify each peptide that is associated with a retention time that is within the elution time period, which then indicates that-if the peptide is present in the sample—it would be present in the portion (as opposed to another portion associated with a different elution time period).

A mass-spectrometry analysis can then be performed on the portion of the eluted sample to generate a mass spectrum. A reference peak location (m/z) for each of the peptides can be associated with a retention time within the elution time period. The mass spectrum of the eluted portion can be analyzed using the reference peak locations to determine which (if any) of the peptides are present within the portion of the sample. The portion collection and assessment (e.g., using mass-spectrum data) can be repeated for one or more other sample portions collected during different elution time periods. The peptides identified for each sample portion can be aggregated to generate an output identifying a plurality of peptides estimated to be present within the particular sample.

Techniques disclosed herein that use a machine-learning model to facilitate building a retention-time library allow the library to be large and/or comprehensive (to the extent that peptides are characterized in the art) without requiring extensive experimental efforts to detect individual peptides' retention times. The comprehensiveness of the library that can be achieved with techniques disclosed herein further improves accuracy of peptide detections that can be performed and the complexity of samples for which peptide-detection can be performed. Advantageously, the present machine-learning model can overcome the computationally intensive and inaccurate problem of experimental methods that includes both pattern recognition and optimization on noisy, ambiguous, and incomplete data, and provide accuracy and efficiency of estimating peptide-retention time from samples including a large number of peptides.

FIG. 1 shows a system 100 for estimating peptide-retention for a sample in accordance with some embodiments of the invention. The system 100 includes a machine-learning computing system 110 for training and running a machine-learning model 115, a chromatography system 160, and a mass spectrometer system 175. One or more chromatography systems (e.g., that can include chromatography system 160) can be used to identify—for each of a first set of peptides—a retention time that indicates when the peptide was eluted from the column relative to a sample-injection time (e.g., thereby indicating a duration of time for the peptide to elute from a separations column). In some embodiments, the retention times can be obtained from one or more private or public database sources. The private or public database sources may be a centralized, standards compliant, data repository for proteomics data.

Training data that includes multiple training data sets can be generated and stored in a training data store 120. Each of the training data sets can correspond to a peptide and can be defined to include the retention times and characteristics and/or identities of the first set of peptides. Each of the training data sets may include one or more training vectors. The training vectors can indicate parameters of the training data for training the machine-learning model 115. For example, the training vectors may indicate, for each amino acid present in the peptide, an identity or characteristic of the amino acid. In some embodiments, each of the training vectors may indicate the length of the peptide, identity of the amino acids within the peptide, mass-to-charge ratio of the amino acids within the peptide, hydrophobicity of the amino acids within the peptide, or combinations thereof.

The machine-learning computing system 110 can use the training data from the training data store 120 to train the machine-learning model 115 (e.g., such that a set of parameters are learned). In some embodiments, the training data may be divided into subsets for training, validation, and testing, respectively. For example, a first subset of the training data sets can be used to train the model, a second subset of the training data sets can be used to test the trained model and a third subset of the training data sets can be used to validate the trained model.

The machine-learning model 115 can include encoder-decoder network. The encoder-decoder network may include an encoder portion and a decoder portion. In some embodiments, the encoder portion comprises a recurrent neural network of multiple layers of long short term memory (LSTM) cells. In particular, the encoder-decoder network can be configured to receive, as input, a characteristic and/or identity of each amino acid within a peptide, and can generate, as an output, an estimated retention time for the peptide. For example, the model can be configured to receive, as input, one or more variable-length that identify or characterize amino acids. The encoder-decoder network comprises of two parts: an encoder and a decoder. The encoder network is that part of the network that takes the input and maps it to an encoded representation. The encoded representation is then used by the decoder network to generate an output.

A recurrent neural network (RNN) can include a network of nodes and a set of connections between the nodes that form a directed graph. A particular type of RNN includes LSTM units, which can use time delays and/or feedback loops to create controlled states. An LSTM network (defined as an RNN network that includes one or more LSTM units) can enable learning long-term and short-term dependencies (e.g., the gap between where relevant information was discovered in the network and the point where the relevant information is needed in the network to predict the next object). A "long short term memory cell" can include a unit of a recurrent neural network comprising multiple interacting layers that can keep a piece of information for long or short periods of time during work and protect the gradient inside the cell from detrimental changes during the training. For example, an LSTM cell may comprise three gates (input, forget, output), and a cell unit. The gates may be configured to use a sigmoid activation, while input and cell state may be transformed with the hyperbolic tangent, or tanh function. A "gradient recurrent unit cell" can include a unit of a recurrent neural network that modulates the flow of information inside the unit, however, without having a separate memory cell. The activation of the GRU cell at time I can trigger a linear interpolation between the previous activation and the candidate activation where an update gate decides how much the unit updates its activation, or content. This procedure of taking a linear sum between the existing state and the newly computed state is similar to the LSTM cell. The GRU cell, however, does not have any mechanism to control the degree to which its state is exposed, but exposes the whole state each time.

In some embodiments, the encoder network maps a variable-length input, e.g., from the training data, to a fixed-dimensional vector representation, and the decoder network maps the vector representation to a peptide-retention time. In some embodiments, the encoder appends one or more metadata features to an encoder output. The decoder portion decodes the encoder output into the peptide-retention time based on the metadata features. The one or more metadata features can include at least one of the following: column-type, fragmentation method, fragmentation energy, gradient, and time.

In some embodiments, weights and/or biases of the encoder-decoder network may be adjusted in response to the training process. In some embodiments, adjusting the weights and/or biases includes feeding the gradient of the loss function calculated in step into an optimization process, which updates or adjusts the weights and/or biases for the one or more nodes, cells, neurons, or layers in an attempt to minimize the loss function. Accordingly, as the encoder-decoder network is trained, the nodes, cells, or neurons in the intermediate layers organize themselves in such a way such that the different nodes, cells, or neurons learn to recognize different characteristics of the total input space. After training, the nodes, cells, or neurons in the hidden layers of the network can respond with an active output if the new input contains a pattern that resembles a feature that the individual nodes, cells, or neurons have learned to recognize during their training. Optionally, the training process may further include a pre-training process to determine initial weights and biases for the one or more nodes, cells, neurons, or layers that approximate the final solution to avoid potential problems with the backpropagation of the error values. In certain embodiments, the encoder portion and the decoder portion initially share weights and biases (prior to training), use different sets of weights and biases, or include a combination of similar and different weights and biases.

The machine-learning computing system 110 can execute the trained machine-learning model 125 to estimate retention times of a second set of peptides to output an estimated retention time for each of a set of other peptides. The second set of peptides can be obtained from an other data sets store 130. For example, the trained machine-learning model 125 can receive a set of other data sets from the other data sets store 130—each representing another peptide. Each of the set of other data sets can include amino-acid data that indicates, for each amino acid present in the other peptide, an identity or characteristic of the amino acid. The trained machine-learning model 125 can process the other data set(s) to output an estimated retention time for each of the set of other peptides. The machine-learning computing system 110 can store pair-wise associations between identifier of the set of other peptides and the estimated retention times within a retention-time library data structure 135. The retention-time library data structure 135 may further include associations between peptide identifiers and retention times from the training data sets.

The retention-time library data structure 135 can be used to detect one or more peptides within a sample using one or more mass spectra generated using the sample. More specifically, a sample can be injected into an injection port 165 of the chromatography system 160. One or more portions of the sample that are eluted from a chromatography column of the chromatography system 160 within each of one or more pre-identified time periods can be collected by a fraction collector 170. The retention time of the one or more portions of the sample that are eluted from a chromatography column of the chromatography system 160 can stored in a chromatography column data structure 140. With respect to each of the one or more pre-identified time periods, the retention-time library data structure 135 can be queried to identify a subset of the peptides represented in the library where each peptide in the subset is associated with a retention time within the pre-identified time period stored in the chromatography column data structure 140. With regard to each peptide identified in the subset, the peptide's inclusion in the subset indicates that—if the peptide is present in the sample—it would be present in the portion (as opposed to another portion associated with a different elution time period).

Mass-to charge ratios (m/z) can be identified for each peptide in the subset(s). For each of the one or more collected portions, the mass spectrometer system 175 can perform a mass spectrometry analysis on the portion to generate a mass spectrum. The mass spectrometer system 175 can include an ionizer 180, a mass analyzer 185, and a detector 190, to perform a mass spectrometry analysis on the portion to generate a mass spectrum. The mass spectrum data for each of the one or more collected portions can be stored in a mass spectra data store 150. The machine-learning computing system 110 can access the mass spectrum data from the mass spectra data store 150, perform a peak detection, compare the mass-to-charge ratio of each detected peak to the mass-to-charge ratios identified for the corresponding subset of peptides, and determine which (if any) of the subset of peptides are present in the sample based on the comparison. The peptides identified for each sample portion can be aggregated using an output generator 145 to generate an output identifying a plurality of peptides estimated to be present within the particular sample.

In some embodiments, the training data sets are pre-processed by the machine-learning model. In various embodiments, the pre-processing includes identifying peptides based on the identity or characteristics of the amino acids within the peptide. For example, twenty-two amino acids are naturally incorporated into peptide chains and are called proteinogenic or natural amino acids. Of these twenty-two amino acids, twenty are encoded by the universal genetic code. The remaining two, selenocysteine and pyrrolysine, are incorporated into proteins by unique synthetic mechanisms. When two or more amino acids combine to form a peptide, the elements of water are removed, and what remains of each amino acid is called an amino acid residue. Amino-acid residues are therefore structures that lack a hydrogen atom of the amino group (—NH—CHR—COOH), or the hydroxyl moiety of the carboxyl group ($NH_2$—CHR—CO—), or both (—NH—CHR—COO—); all units of a peptide chain are therefore amino-acid residues. The amino acid residue in a peptide that has an amino group that is free, or at least not acylated by another amino-acid residue (it may, for example, be acylated or formylated), is called the N-terminal; it is at the N-terminus. The amino acid residue that has a free carboxyl group, or at least does not acylate another amino-acid residue (it may, for example, be acylate ammonia to give-NH—CHR—CO—$NH_2$) is called the C-terminal; it is at the C-terminus.

Furthermore, some peptide or protein chains undergo post-translational modification. Post-translational modification refers to the covalent and generally enzymatic modification of proteins during or after protein biosynthesis. Post-translational modifications can occur on the amino acid side chains or at the peptide's C- or N-termini. Post-translational modifications can extend the chemical repertoire of the twenty standard amino acids by modifying an existing functional group or introducing a new one such as phosphate. Phosphorylation is a very common mechanism for regulating the activity of enzymes and is one of the most common post-translational modifications.

In some embodiments, the training data can be represented by a N×L matrix, where L is the length of the peptide and N is the number of vectors for each amino acid in the peptide. For example, the vectors can include twenty fields (or a few more for synthetic and/or modified amino acids) for one-hot-encoded amino-acid types, and a field for hydrophobicity for the associated amino-acid type.

In some embodiments, the machine-learning computing system 110 may comprise one or more processors. The processors may include one or more processors, microprocessors, or specialized dedicated processors that include processing circuitry operative to interpret and execute computer readable program instructions, such as program instructions for controlling the operation and performance of one or more of the various other components of system 100 for implementing the functionality, steps, and/or performance of the present invention. In certain embodiments, the one or more processors interpret and execute part of all of one or more processes, steps, functions, and/or operations described herein, which may be operatively implemented by the computer readable program instructions.

The storage device may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of machine-learning computing system 110 in accordance with the different aspects of the present invention. In embodiments, storage device may store operating system, application programs, and program data in accordance with aspects of the present invention.

Figure 2:
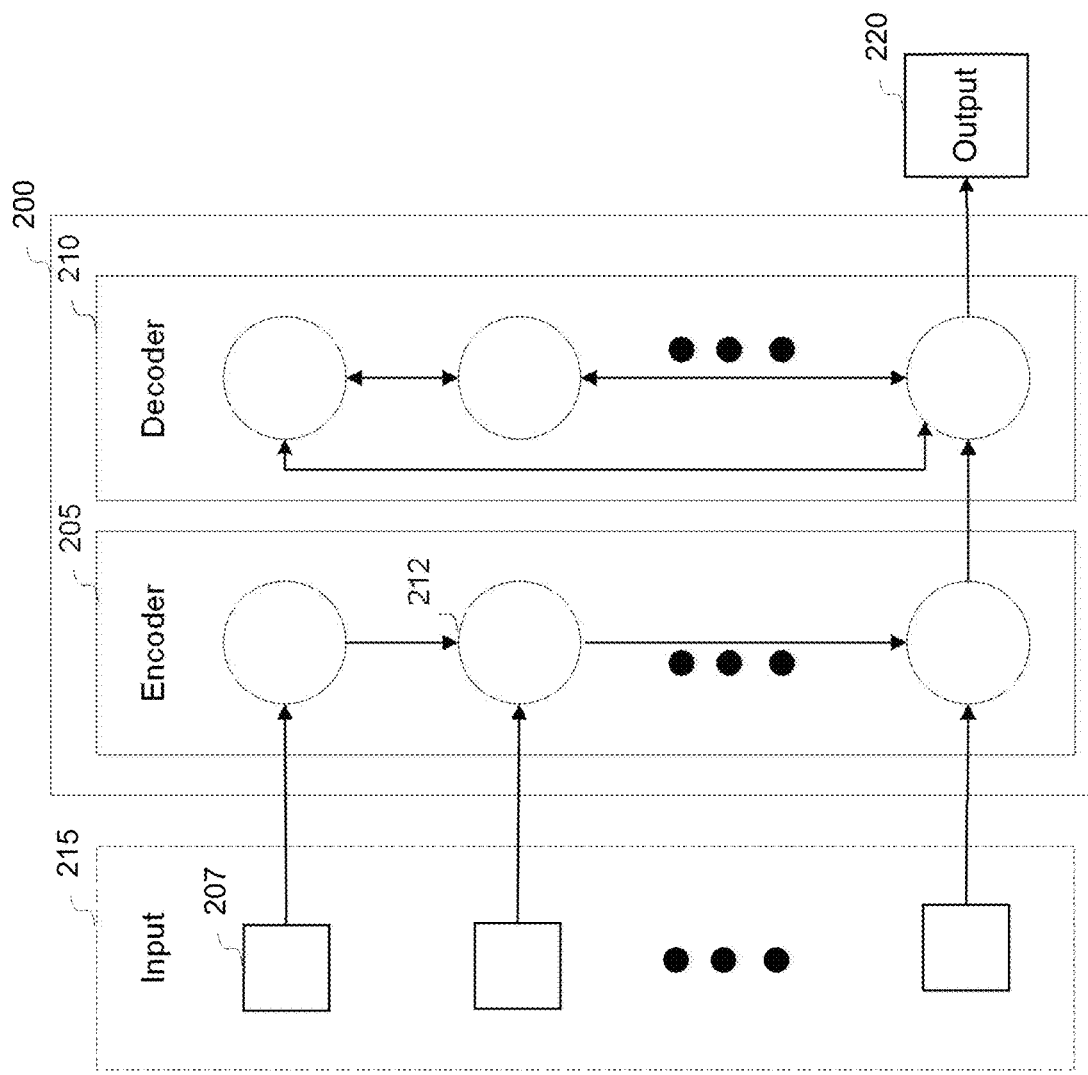
FIG. 2 shows a schematic representation of an encoder-decoder network in accordance with some embodiments of the invention.

FIG. 2 shows a schematic representation of an encoder-decoder network 200 of the machine-learning model in accordance with some embodiments of the invention. As shown in FIG. 2, the encoder-decoder network 200 may comprise an encoder portion 205 and a decoder potion 210. The encoder-decoder network 200 can receive input data 215, which can include multiple input values 207. Each input value can include (for example) a real number, an integer, a category identifier, etc. In some instances, each of some or all input variables correspond to a single amino acid in a peptide (e.g., indicating an identity of the amino acid or a characteristic of the amino acid, such as a hydrophobicity). In some instances, input data 215 that corresponds to a single peptide includes a set of input values 207, where a quantity of the values within the set is at least (or is equal to) a number of amino acids within the peptide (or a multiple of the number). Input data 215 may include a vector, matrix, array or string. Given that individual values can correspond to individual amino acids, which have particular positions within the peptide, the values can have a particular order and be characterized as being sequential data.

The encoder portion 205 can include a recurrent neural network and/or can include one or more LSTM units. In some embodiments, the encoder portion 205 can be configured to receive input data 215 that is of a variable length or size, thereby indicating that a size of one input data processed by the encoder-decoder network 200 can be different than a size of other input data.

The encoder portion 205 can transform the input data into an encoded representation (fixed-dimensional vector representation) of the input data. The encoder portion 205 can include a set of nodes or neurons 212—each of which can be configured to perform one or more predefined operations on at least part of the input data 215 (or a processed version thereof). The predefined operations can be defined using one or more parameters, which can be learned using training data. It will be appreciated that the data processed at each encode node can include one or more input values 207 (e.g., raw input values) and/or one or more results generated by another part of the encoder-decoder network 200 (e.g., by another encoder node).

The encoder portion 205 is configured such that each training sequence can be provided forwards and backwards to two separate recurrent neural networks (RNNs), outputs of which are concatenated with metadata and then connected to the same output layer. Unlike conventional RNNs, bidirectional RNNs utilize both the previous and future context, by processing the data from two directions with two separate hidden layers. One layer processes the input data in the forward direction, while the other processes the input in the reverse direction. The output of a current time step is then generated by concatenating a vector from each hidden layer. Accordingly, for every point in a given sequence, the encoder portion 205 has complete, sequential information about all points before and after it, and is capable of reading the input sequence, one time step at a time, to obtain the encoded representation. Also, because the encoder portion 205 is free to use as much or as little of this context as necessary, there is no need to find a (task-dependent) time-window or target delay size.

The encoder-decoder network 200 may further comprise a decoder portion 210 including a fully-connected network. The decoder portion 210 is configured such that the encoded representation obtained, for example, from each training data set can be passed through the decoder portion 210 to obtain a variable-length target sequence of amino acids. In some embodiments, the decoder portion 210 takes the encoded representation and maps the encoded representation back to a variable-length target sequence of amino acids. In certain embodiments, the variable-length target sequence of amino acids is provided as a multi-dimensional data set of amino acids types (e.g., twenty proteinogenic or natural amino acids) and probability of each amino acid type in each position of the sequence.

Figure 3:
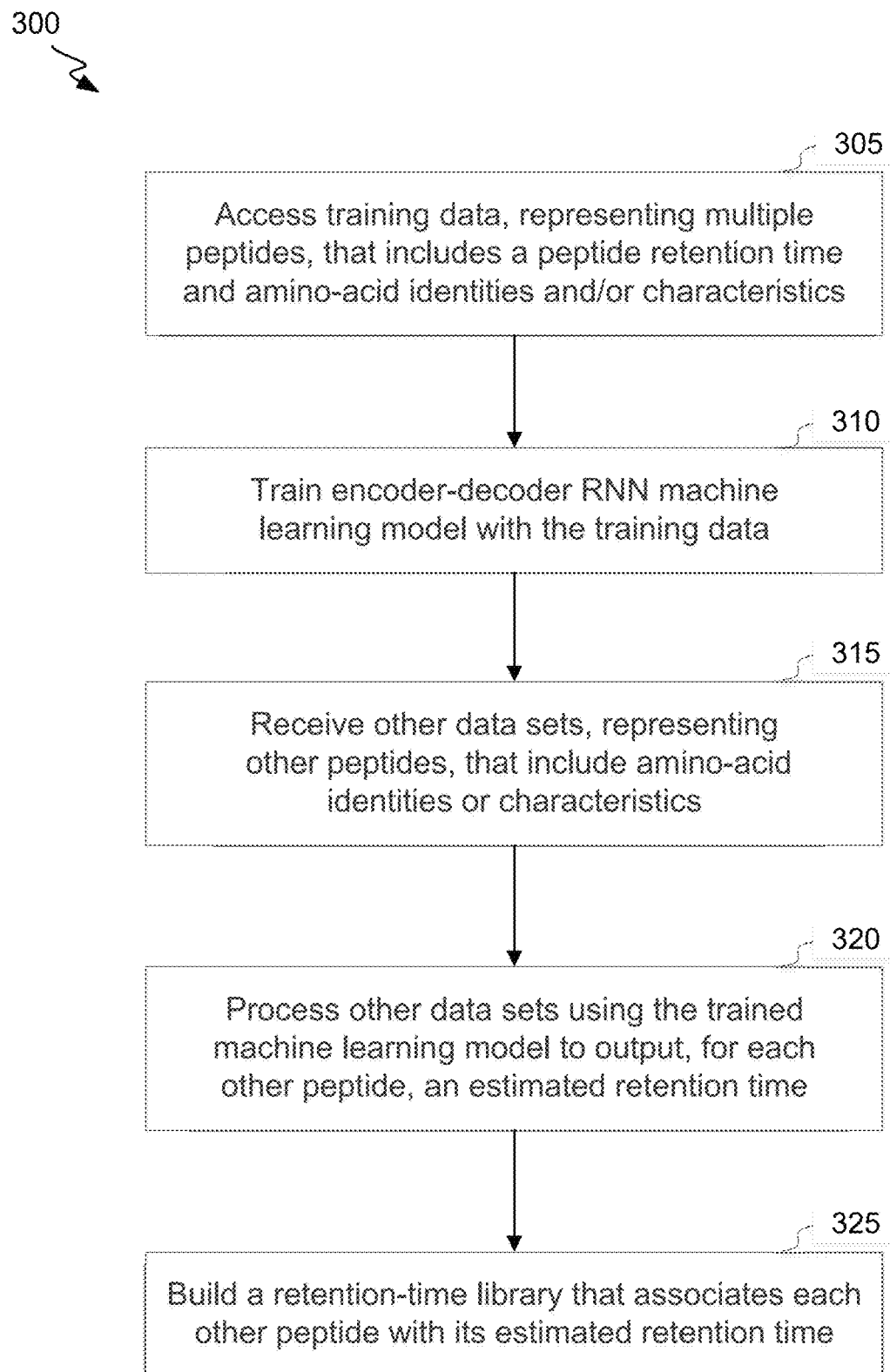
FIG. 3 illustrates a process for building a retention-time library using a machine-learning model trained using training data in accordance with some embodiments of the invention.

FIG. 3 illustrates a process 300 for building a retention-time library using a machine-learning model trained using training data sets. Process 300 begins at block 305, where training data, representing multiple peptides, is accessed. The training data may correspond to a peptide retention time and amino acid identities and/or characteristics for the amino acids present in the peptide. For example, the training data can correspond to a peptide and include amino-acid data that indicates an identity and hydrophobicity of each amino acid present in the peptide. Each of training data sets can further include retention time for the peptide that indicates how long it takes for the peptide to elute from a separations column (e.g., liquid chromatography column) relative to an injection time.

At block 310, the machine-learning model may trained using the training data. The machine-learning model can include an encoder-decoder model. The encoder and/or the decoder can include a neural network. A neural network in the encoder can include a recurrent neural network and one or more long-short term memory (LSTM) cells configured to process ordered information. A neural network in the decoder can include a dense network, such as a fully-connected network. In some instances, one or both of the encoder and decoder includes multiple layers. For example, the encoder may include between two and five layers, and/or the decoder may also include between two and five layers. The machine-learning model can be trained using the training data to define a set of parameter values. For example, the parameters can include one or more weights, coefficients, magnitudes, thresholds and/or offsets. The parameters can include one or more parameters for a regression algorithm, encoder and/or decoder. The training can, for example, use a predefined optimization algorithm.

At block 315, the trained machine-learning model can receive other data sets representing other peptides. Each of the other data sets can include amino-acid data that indicates, for each amino acid present in the other peptide, an identity or characteristic of the amino acid. At block 320, the trained machine-learning model can process the other data sets to output an estimated retention time for each of the other peptides. The trained machine-learning model can be configured with defined hyperparameters and learned parameters. At block 325, a retention-time library can be built or updated to include, for each of the other data sets, an association between an identifier of the peptide represented by the other data set and the estimated retention time. The retention-time library may further include associations between peptide identifiers and retention times from the training data sets.

Figure 4:
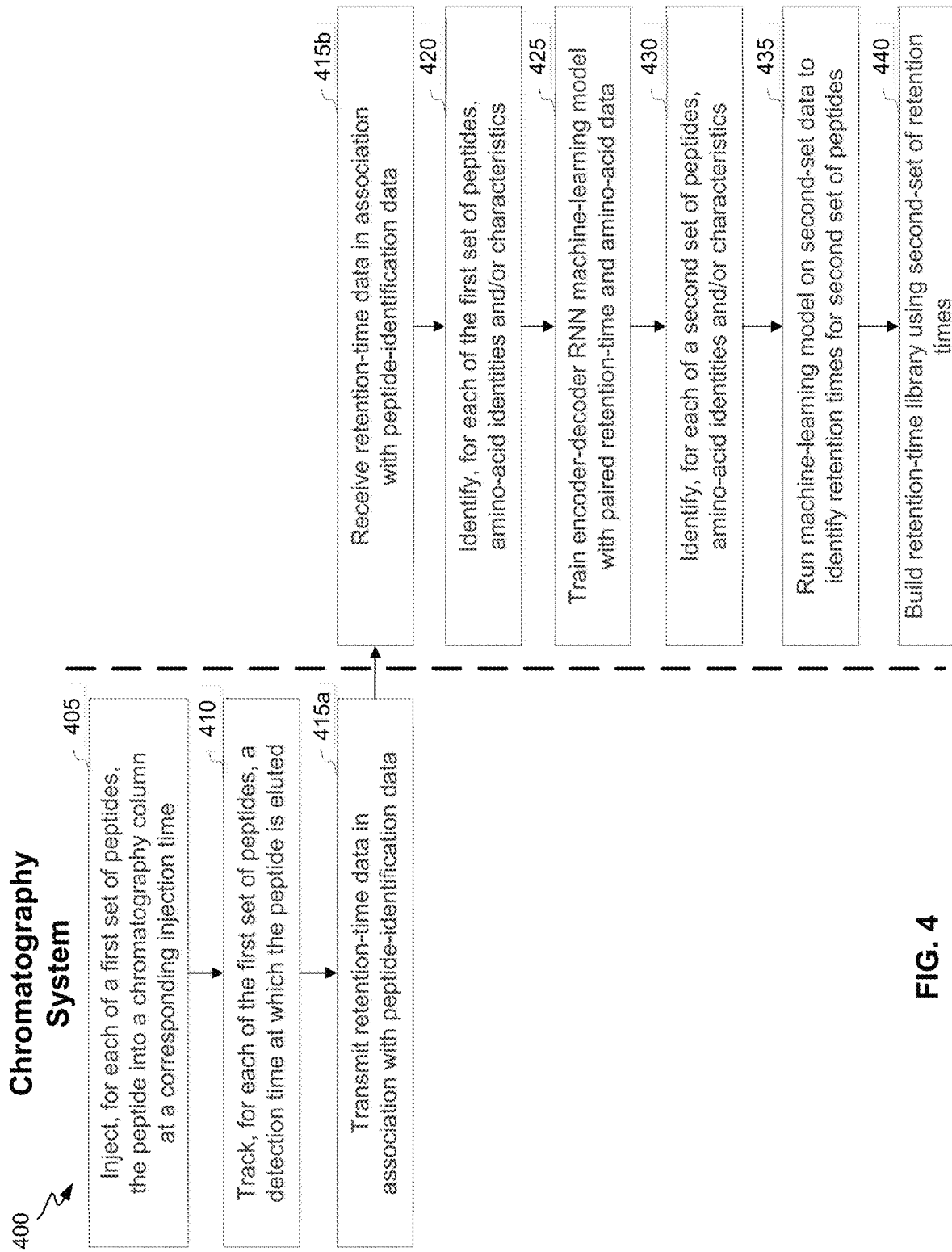
FIG. 4 illustrates a process of training a machine-learning computing system in accordance with some embodiments of the invention.

FIG. 4 shows an exemplary process 400 for training a machine-learning computing system according to embodiments of the disclosure. At block 405, a first set of peptides may be injected into the chromatography column at a corresponding injection time. The first set of peptides may comprise a plurality of known peptides, such that peptide-identification data for the peptides are known. At block 410, for each set of peptides that is injected into the chromatography column, the peptide is tracked to determine a retention time. For example, the chromatography system can track the time each set of peptides takes to elute from the chromatography column. More specifically, the chromatography system measures how long each set of peptides takes to elute from the column relative to the injection time. Each set of peptides can be collected from the column. At block 415a, the chromatography system can then transmit 415a the retention time data in association with the peptide-identification data to a machine-learning computing system. It will be appreciated that the retention-time data may (in some instances) be availed to the machine-learning computing system using one or more other techniques. For example, the chromatography system may present the retention time(s), such that a user can input them (e.g., with identifications of corresponding peptides) to the machine-learning computing system. As another example, the machine-learning computing system may request the retention-time data from a cloud server system and/or cloud database, which may have received uploads of the retention-time data from one or more chromatography systems and/or other computing devices.

At block 415b, the machine-learning computing system can receive the transmitted retention-time data from the chromatography system. The retention-time data can indicate a peptide identify (and/or amino-acid identities) corresponding to each retention time. When amino-acid identities are not included in the retention-time data, the machine-learning computing system can look up the ordered amino-acid identities. At block 420, for each set of peptides, the machine-learning computing system can generate amino-acid data that indicates—for each amino acid included in the peptide—an identity of the amino acid and/or one or more characteristics of the amino acid. A training data set for each peptide can be defined to include the amino-acid data and the retention time. At block 425, the machine-learning model can be trained with the paired retention-time data and the amino-acid identity and/or characteristics data. Training the machine-learning model can include using supervised or semi-supervised learning to derive values for each of a set of parameters (e.g., values for LSTM gates, bias neurons, inter-neuron weights, etc.).

At block 430, for a second set of peptides, an input data set can be defined that includes an identity and/or one or more characteristics of the amino acids within each peptide. At block 435, the trained machine-learning model can be executed to an estimate peptide-retention time for each of the peptides in the second set of peptides. At step 440, a retention-time library can be built using the second set of retention-time data. For example, a computing system can then store, for each peptide of the second set of peptides, an identifier of the peptide in association with the corresponding estimated retention time in a retention-time library, which can be configured to be a queryable data structure.

Figure 5:
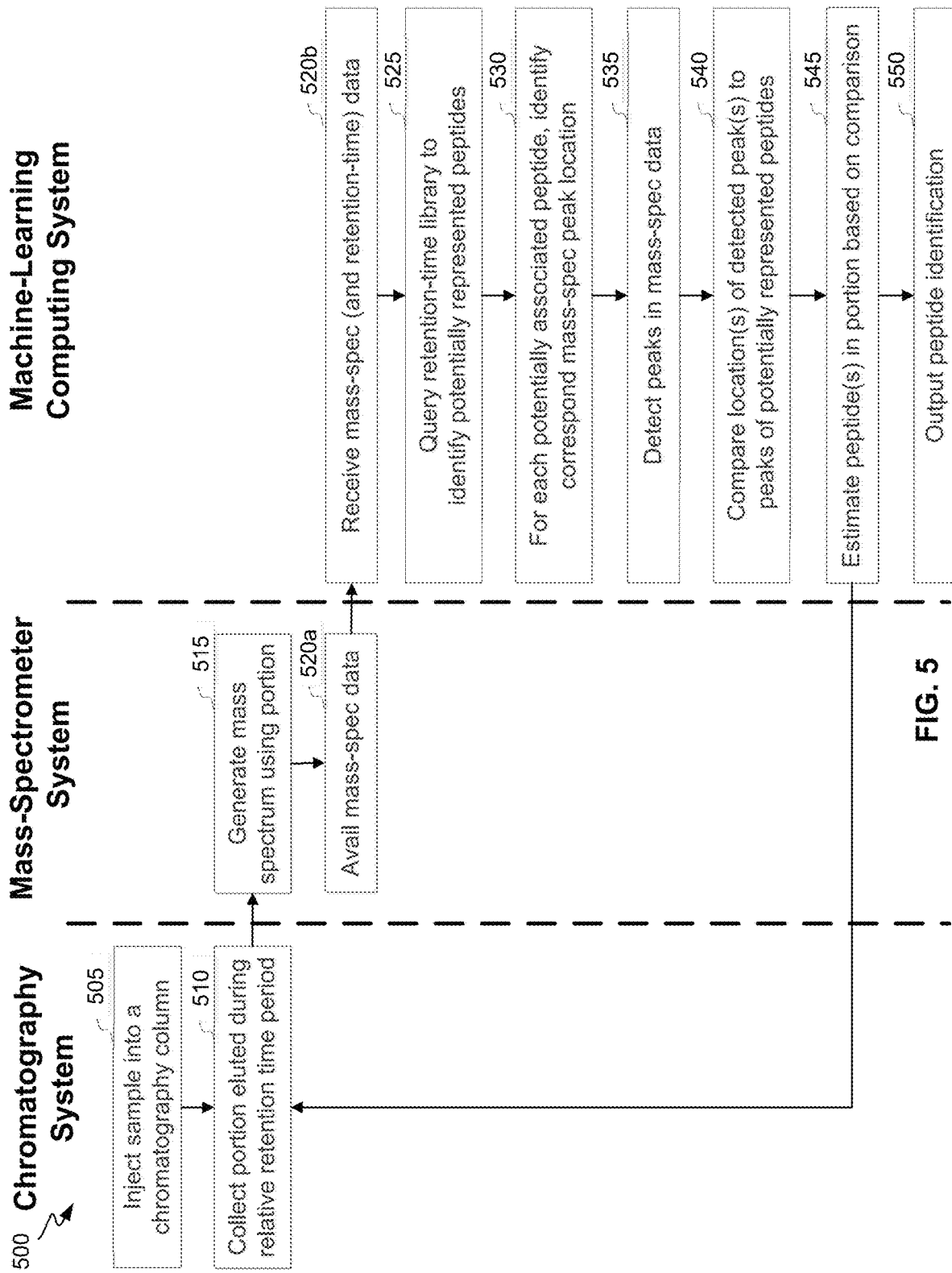
FIG. 5 illustrates a process for using a trained a machine-learning model to estimate which peptides are within a sample in accordance with some embodiments of the invention.

FIG. 5 shows an exemplary process 500 for using a trained a machine-learning model for using estimated peptide-retention times estimated by a machine-learning model to estimate which peptides are within a sample according to embodiments of the disclosure. At block 505, a sample may be injected into a chromatography column. At block 510, a portion of the sample that is eluted from the chromatography column is collected. The time period during which the portion was eluted can be identified as a collection time period for the portion. In some instances, one or more collection time periods can be pre-identified, and a portion can be separately collected during each of the one or more collection time periods and separately analyzed.

At block 515, the collected portion of the sample can be analyzed in a mass-spectrometer system. The mass-spectrometer system can generate a mass spectrum, which can identify a relative intensity associated with each of a set of mass-to-charge. In some instances, the mass-spectrometer system detects each of one or more peaks within the mass spectrum and identifies the mass-to-charge ratio and relative intensity associated with each peak. Mass-spectrum data can include the mass spectrum and/or can include peak data that includes the mass-to-charge ratio of each peak and potentially also the relative intensity of each peak. At block 520*a*, the mass-spectrum data for the portion of the sample can be availed to the machine-learning computing system, which can receive the mass-spectrum data at block 520*b*.

At block 525, the machine-learning computing system can query the retention-time library to identify each peptide that is associated with a retention time that is within the collection time period, which then indicates that-if the peptide is present in the sample—it would be present in the portion (as opposed to another portion associated with a different elution time period). At block 530, for each these identified peptides, the machine-learning computing system can then identify the mass-to-charge ratio associated with the peptide. Each of these mass-to-charge ratios can be characterized as a reference peak location.

At block 535, one or more peaks represented in the mass-spectrum data are detected. Performing the peak detection can include (for example) identifying relative intensities that exceed a predefined threshold, taking a derivative of the spectrum and identifying x-positions at which the derivative exceeds a predefined threshold, identifying local maxima in combination with threshold analyses, and so on.

At block 540, the location (i.e., mass-to-charge ratio) of each of the detected peaks is compared with the locations of each of the reference peaks. In some instances, the comparison includes determining whether a location of a detected peak is the same as a location of a reference peak. In some instances, the comparison includes determining whether a location of a detected peak is within a predefined range from a location of a reference peak.

At block 545, the machine-learning model estimates which peptides are present within the sample based on the comparison. Some blocks (e.g., blocks 510-545) can be repeated for one or more other portions of the sample. It will be appreciated that the block repetition need not be performed in the order presented. For example, block 510 may be repeated a number of times to collect different sample portions. After all of the portion collections, block 515 may be repeated a number of times to generate a mass spectrum for each portion. The mass-spectrum data may then be availed in bulk to the machine-learning computing system, which may then perform blocks 525-545 with respect to each portion in parallel or serially.

At block 550, the peptides identified for each sample portion can be aggregated to generate an output identifying a plurality of peptides estimated to be present within the particular sample. The peptide identification can be output via (for example) a local presentation or a transmission of data.

Example

Figure 6:
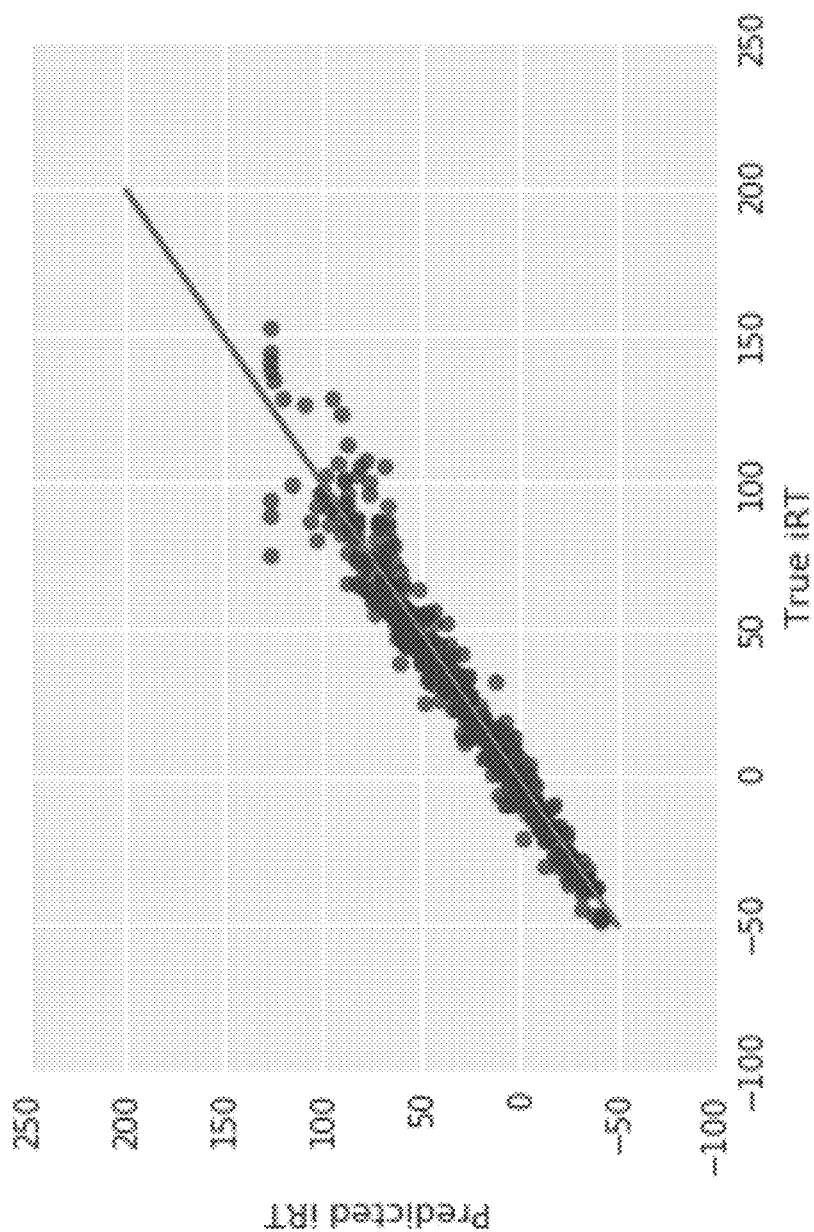
FIG. 6 shows data indicating a quality of retention-time estimates generated using a machine-learning model in accordance with some embodiments of the invention.

FIG. 6 shows data indicating a quality of retention-time estimates generated using a machine-learning model. In this instance, a machine-learning model was configured to include an encoder portion and decoder portion. The encoder portion included an RNN including LSTM layers. Specifically, the encoder portion included a bidirectional RNN having two LSTM layers. The decoder portion included a fully connected dense neural network that included two layers. The machine-learning model was configured to receive an input data set that identified a hydrophobicity for each amino acid within a peptide and to output an estimated retention time. The machine-learning model was trained with a training data set that corresponded to 3,500 peptides.

The trained machine-learning model was then used to generate an estimated retention time for each of other peptides (using a vector that identified a hydrophobicity of each amino acid in the peptide as input). In FIG. 6, each dot corresponds to one of the other data sets. The y-value of the dot indicates the estimated retention time generated by the machine-learning model, and the x-value of the dot indicates the experimentally derived true retention time for the peptide. The correspondence between the estimated and true values was high.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A method comprising:
    accessing training data comprising a plurality of training data sets, each training data set of the plurality of training data sets respectively corresponding to a peptide of a first set of peptides and comprising:
        one or more training vectors that indicate, for each amino acid present in a corresponding peptide, an identity or characteristic of the amino acid, and
        a retention time for the corresponding peptide, the retention time corresponding to a duration of time for the corresponding peptide to elute from a separations column;
    training a machine-learning model comprising a plurality of neural networks, by using the plurality of training data sets to determine a set of parameters for a trained machine-learning model, the machine-learning model comprising an encoder-decoder network including an encoder portion and a decoder portion, wherein the encoder portion comprises a recurrent neural network and the decoder portion comprises a fully-connected neural network,
    the training comprising, for each training data set:
        inputting, to the encoder portion, the one or more training vectors, to generate an encoded representation for the one or more training vectors,
        appending, by the encoder portion, the encoded representation with metadata comprising one or more metadata features, and decoding, by the decoder portion, the encoded representation based on the one or more metadata features, to provide an estimated retention time for the peptide, wherein the metadata comprises one or more of column-type, fragmentation method, fragmentation energy, gradient, or time;

receiving a plurality of other data sets, each of the plurality of other data sets respectively representing other peptide from a second set of peptides and comprising one or more input vectors that indicate, for each amino acid present in a corresponding other peptide, an identity or characteristic of the amino acid;

processing, for each other data set of the plurality of other data sets, the one or more input vectors of the other data set using the trained machine-learning model to output an estimated retention time for the corresponding other peptide;

for each other data set, storing, in a memory, an identifier of the corresponding other peptide in association with the estimated retention time for the corresponding other peptide, to form a data structure comprising a plurality of pairs, each of the plurality of pairs comprising the corresponding other peptide associated with the estimated retention time for that other peptide;

injecting a sample into a chromatography column, the sample comprising a plurality of sample portions, each sample portion of the plurality of sample portions including one or more peptides;

identifying a set of time periods, each time period of the set of time periods corresponding to a respective elution time duration of a corresponding sample portion and has a start time at a time of injecting the sample into the chromatography column and a stop time at a time when the corresponding sample portion was eluted;

comparing the time periods of the set of time periods to the estimated retention times stored in the data structure;

based on the comparing, identifying a set of specific estimated retention times, each specific retention time of the set of specific estimated retention times being within one of the time periods of the set of time periods;

for each sample portion, retrieving, from the memory, one or more identifiers of one or more other peptides, the one or more identifiers being stored in association with one or more specific estimated retention times, respectively, of the set of specific estimated retention times;

generating a set of reference peptides to include the one or more other peptides;

performing a mass-spectrometry analysis on the sample portion associated with a corresponding time period, to generate a mass spectrum of the sample portion, the mass spectrum respectively identifying one or more characteristics of the one or more peptides included in the sample portion; and identifying the one or more peptides based on the identified one or more characteristics and characteristics respectively associated with the reference peptides.

2. The method of claim 1, further comprising:
for each time period of the set of time periods:
identifying, for each peptide of the set of reference peptides, a mass-to-charge variable associated with the peptide; and
generating, based on the mass spectrum and the identified mass-to-charge variables for the set of reference peptides, an indication as to which of the set of reference peptides have been detected in the sample portion;

aggregating the indications across the set of time periods to generate an output identifying a plurality of peptides estimated to be present within the sample; and
outputting the output.

3. The method of claim 1, wherein the one or more training vectors indicates, for each amino acid present in the peptide, an identity of the amino acid, a hydrophobicity of each amino acid, or combinations thereof.

4. The method of claim 1, wherein the recurrent neural network comprises one or more long-short term memory layers.

5. The method of claim 1, wherein the recurrent neural network comprises a bidirectional recurrent neural network.

6. The method of claim 1, wherein the decoder portion comprises one or more fully-connected neural network layers.

7. The method of claim 1, wherein the encoder-decoder network comprises at least two long-short term memory layers and at least two fully-connected neural network layers.

8. The method of claim 1, wherein the encoder-decoder network comprises between one and five encoder layers and between one and five decoder layers.

9. A system comprising:
a computer system comprising one or more data processors; and a non-transitory computer readable storage medium; and
a chromatography-mass spectrometry system coupled to the computer system,
wherein the non-transitory computer readable storage medium contains instructions that, when executed by the one or more data processors, cause the one or more data processors to perform actions including:
accessing training data comprising a plurality of training data sets, each training data set of the plurality of training data sets respectively corresponding to a peptide of a first set of peptides and comprising:
one or more training vectors that indicate, for each amino acid present in a corresponding peptide, an identity or characteristic of the amino acid, and
a retention time for the corresponding peptide, the retention time corresponding to a duration of time for the corresponding peptide to elute from a separations column;
training a machine-learning model comprising a plurality of neural networks, by using the plurality of training data sets to determine a set of parameters for a trained machine-learning model, the machine-learning model comprising an encoder-decoder network including an encoder portion and a decoder portion, wherein the encoder portion comprises a recurrent neural network and the decoder portion comprises a fully-connected neural network,
the training including, for each training data set:
inputting, to the encoder portion, the one or more training vectors, to generate an encoded representation for the one or more training vectors,
appending, by the encoder portion, the encoded representation with metadata comprising one or more metadata features, and
decoding, by the decoder portion, the encoded representation based on the one or more metadata features, to provide an estimated retention time for the peptide, wherein the metadata comprises one or more of column-type, fragmentation method, fragmentation energy, gradient, or time;

receiving a plurality of other data sets, each of the plurality of other data sets respectively representing other peptide from a second set of peptides and comprising one or more input vectors that indicate, for each amino acid present in a corresponding other peptide, an identity or characteristic of the amino acid;

processing, for each other data set of the plurality of other data sets, the one or more input vectors of the other data set using the trained machine-learning model to output an estimated retention time for the corresponding other peptide;

for each other data set, storing, in a memory, an identifier of the corresponding other peptide in association with the estimated retention time for the corresponding other peptide, to form a data structure comprising a plurality of pairs, each of the plurality of pairs comprising the corresponding other peptide associated with the estimated retention time for that other peptide;

identifying a set of time periods, each time period of the set of time periods corresponding to a respective elution time duration of a corresponding sample portion a plurality of sample portions of a sample injected into a chromatography column, wherein each sample portion of the plurality of sample portions includes one or more peptides and has a start time at a time of injecting the sample into the chromatography column and a stop time at a time when the corresponding sample portion was eluted;

comparing the time periods of the set of time periods to the estimated retention times stored in the data structure;

based on the comparing, identifying a set of specific estimated retention times, each specific retention time of the set of specific estimated retention times being within one of the time periods of the set of time periods;

for each sample portion, retrieving, from the memory, one or more identifiers of one or more other peptides, the one or more identifiers being stored in association with one or more specific estimated retention times, respectively, of the set of specific estimated retention times;

generating a set of reference peptides to include the one or more other peptides; and receiving, from the chromatography-mass spectrometry system, a mass spectrum from the sample portion associated with a corresponding time period, the mass spectrum respectively identifying one or more characteristics of the one or more peptides included in the sample portion, and wherein the actions further include:
identifying the one or more peptides based on the identified one or more characteristics and characteristics respectively associated with the reference peptides.

10. The system of claim 9, wherein the actions further include:
for each time period of the set of time periods:
identifying, for each peptide of the set of reference peptides, a mass-to-charge variable associated with the peptide; and
generating, based on the mass spectrum and the identified mass-to-charge variables for the set of reference peptides, an indication as to which of the set of reference peptides have been detected in the sample portion;
aggregating the indications across the set of time periods to generate an output identifying a plurality of peptides estimated to be present within the particular sample; and
outputting the output.

11. The system of claim 10, wherein the chromatography-mass spectrometry system comprises:
a sample injection port that injects the sample into the chromatography column; and
a fraction collector that, for each time period of the set of time periods, collects the sample portion of the sample that was eluted from the chromatography column; and
a mass spectrometer that includes an ion source, a mass analyzer and a detector, wherein the mass spectrum is generated by:
using the ion source to convert part of the sample portion of the sample into a set of ions;
using the mass analyzer to sort the set of ions according to corresponding mass-to-charge ratios; and
using the detector to detect, for each of a set of mass-to-charge ratios, an intensity based on the sorted set of ions.

12. The system of claim 9, wherein the one or more training vectors indicates, for each amino acid present in the peptide, an identity of the amino acid, a hydrophobicity of each amino acid, or combinations thereof.

13. The system of claim 9, wherein the recurrent neural network comprises one or more long-short term memory layers.

14. The system of claim 9, wherein the recurrent neural network comprises a bidirectional recurrent neural network.

15. The system of claim 9, wherein the decoder portion comprises one or more fully-connected neural network layers.

16. The system of claim 9, wherein the encoder-decoder network comprises at least two long-short term memory layers and at least two fully-connected neural network layers.

17. The system of claim 9, wherein the encoder-decoder network comprises between one and five encoder layers and between one and five decoder layers.

* * * * *